US007182944B2

(12) United States Patent
Bankiewicz

(10) Patent No.: US 7,182,944 B2
(45) Date of Patent: Feb. 27, 2007

(54) METHODS OF INCREASING DISTRIBUTION OF NUCLEIC ACIDS

(75) Inventor: Krys Bankiewicz, Piedmont, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/132,681

(22) Filed: Apr. 25, 2002

(65) Prior Publication Data

US 2002/0187127 A1   Dec. 12, 2002

Related U.S. Application Data

(60) Provisional application No. 60/286,308, filed on Apr. 25, 2001.

(51) Int. Cl.
*A01N 63/00* (2006.01)
*A61K 48/00* (2006.01)

(52) U.S. Cl. .................................................... 424/93.2
(58) Field of Classification Search ............... 424/93.2; 435/455, 456; 514/44
See application file for complete search history.

(56) References Cited

U.S. PATENT DOCUMENTS 5,922,356 A * 7/1999 Koseki et al. ............... 424/489
6,121,246 A * 9/2000 Isner ............................. 514/44
6,309,634 B1 * 10/2001 Bankiewicz et al. ......... 424/93.2
6,410,300 B1 * 6/2002 Samulski et al. ............ 435/239
2002/0068717 A1 * 6/2002 Borrelli ......................... 514/44
2002/0141980 A1 * 10/2002 Bankiewicz et al. ...... 424/93.21

OTHER PUBLICATIONS

Orkin et al., Dec. 7, 1995, "Report and Recommendation of the Panel to Assess the NIH investment in Research and Gene Therapy", issued by the National Institute of Health.*
Handa et al., J Gen Virol. Aug. 2000;81(Pt 8):2077-84.*
Chung et al., Journal of Virology 72:1577-1585, 1998.*
Verma, Nature, vol. 389, pp. 239-242, 1997.*
Provisional Application 60/251,713.*
Anderson et al., Nature, vol. 392, pp. 25-30, 1998.*
Kibbe et al., Arch Surg, 2000:133:191-197.*
Trarbach et al. Cytotherapy, 2000: 2:429-438.*
Hacker et al., Gene Therapy, 2001: 8:966-868.*
Gorecki, Exper Opin. Emerging Drugs, 6:187-198, 2001.*
Agrawal et al., "Cell-cycle kinetics and VSV-G pseudotyped retrovirus-mediated gene transfer in blood-derived CD34+ cells." *Exp. Hematol.* 24(6):738-747 (May 1996).
Bajetto et al., "Glial and Neuronal Cells Express Functional Chemokine Receptor CXCR4 and Its Natural Ligand Stromal Cell-Derived Factor 1." *J Neurochem* 73:2348-2357 (1999).

(Continued)

*Primary Examiner*—Brian Whiteman
(74) *Attorney, Agent, or Firm*—Needle & Rosenberg, P.C.

(57) ABSTRACT

This invention provides a method of increasing the volume of distribution of a nucleic acid encoding a therapeutic agent in a tissue in a subject during localized delivery, comprising administering to the tissue in the subject a nucleic acid encoding a therapeutic agent and a facilitating agent, whereby the inclusion of the facilitating agent increases the volume of distribution of the nucleic acid encoding a therapeutic agent in the tissue.

2 Claims, 1 Drawing Sheet

OTHER PUBLICATIONS

Bankiewicz et al., "Convection-Enhanced Delivery of AAV Vector in Parkinsonian Monkeys; In Vivo Detection of Gene Expression and Restoration of Dopaminergic Function Using Pro-drug Approach." *Exp. Neurol.* 164(1):2-14 (Jul 2000).

Bankiewicz et al., "Practical Aspects of the Development of *ex Vivo* and *in Vivo* Gene Therapy for Parkinson's Disease." *Exp. Neurol.* 144:147-156 (Mar. 1997).

Bernfield et al., "Functions of Cell Surface Heparan Sulfate Proteoglycans." *Annu. Rev. Biochem.* 68:729-777 (1999).

Betz et al., "Gene Transfer to Rodent Brain with Recombinant Adenoviral Vectors: Effects of Infusion Parameters, Infectious Titer, and Virus Concentration on Transduction Volume." *Exp. Neurol.* 150:136-142 (Mar. 1998).

Bhat et al., "Galactosyl ceramide or a derivative is an essential component of the neural receptor for human immunodeficiency virus type 1 envelope glycoprotein gp120." *Proc. Natl. Acad. Sci. USA* 88:7131-7134 (Aug. 1991).

Chung et al., "A27L Protein Mediates Vaccinia Virus Interaction with Cell Surface Heparan Sulfate." *J. Virol.* 72(2)1577-1585 (Feb. 1998).

Cocchi et al., "The V domain of herpes virus lg-like receptor (HIgR) contains a major functional region in herpes simplex virus-1 entry into cells and interacts physically with the viral glycoprotein D." *Proc. Natl. Acad. Sci. USA* 95:15700-15705 (Dec. 1998).

Cunningham et al., "Distribution of AAV-TK Following Intracranial Convection-Enhanced Delivery Into Rats." *Cell Transplant.* 9:585-594 (2000).

Dowd et al., "Heparan Sulfate Mediates bFGF Transport through Basement Membrane by Diffusion with Rapid Reversible Binding." *J. Biol. Chem.* 274(8):5236-5244 (Feb. 19, 1999).

Feyzi et al., "Structural Requirement of Heparan Sulfate for Interaction with Herpes Simplex Virus Type 1 Virions and Isolated Glycoprotein C." *J. Biol. Chem.* 272(40):24850-24857 (Oct. 3, 1997).

Goodman et al. "Recombinant Adeno-Associated Virus-Mediated Gene Transfer Into Hematopoietic Progenitor Cells." *Blood* 84. 84(5):1492-1500 (Sep. 1, 1994).

Hamilton et al., "Heparin coinfusion during convection-enhanced delivery (CED) increases the distribution of the glial-derived neurotropic factor (GDNF) ligand family in rat striatum and enhances the pharmacological activity of neurturin." *Exp. Neurol.* 168(1):155-161 (Mar. 2000).

Immergluck et al. "Viral and cellular requirements for entry of herpes simplex virus type 1 into primary neuronal cells" *J. Gen Virol.* 79(3):549-559 (1998).

Kordower et al., "Clinicopathological Findings Following Intraventricular Glial-Derived Neurotropic Factor Treatment in a Patient with Parkinson's Disease." *Ann. Neur.* 46(3):419-424 (Sep. 1999).

Leiberman et al., "Convection-enhanced distribution of large molecules in gray matter during interstitial drug infusion" *J. Neurosurg.* 82(6):1021-1029 (Jun. 1, 1995).

Matsushita et al., "Adeno-associated virus vectors can be efficiently produced without helper virus." *Gene Ther.* 5(7):938-945 (Jul. 1, 1998).

Mitani et al., "Transduction of Human Bone Marrow by Adenoviral Vector." *Hum. Gene Ther.* 5(8):941-948 (Aug. 1994).

Naidini et al., "In Vivo Gene Delivery and Stable Transduction of Nondividing Cells by a Lentiviral." *Science* 272:263-267 (Apr. 12, 1996).

Peel and Klien, "Adeno-associated virus vectors: activity and applications in the CNS." *J. Neurosci Meth.* 98(2):95-104 (2000).

Qing et al., "Human fibroblast growth factor receptor 1 is a co-receptor for infection by adeno-associated virus 2." *Nat. Am.* 5(1):71-77 (1999).

Qui et al., "The Interaction of Heparin Sulfate and Adeno-Associated Virus 2." *Virology* 269:137-147 (2000).

Schwarzenberger et al., "Target Gene Transfer to Human Hematopoietic Progenitor Cell Lines Through the c-kit Receptor." *Blood* 87(2):472-478 (Jan. 15, 1996).

Summerford and Samulski, "Membrane-Associated Heparan Sulfate Proteoglycan Is a Receptor for Adeno-Associated Virus Type 2 Virions." *J. Virol.* 72(2):1438-1445 (Feb. 1998).

Summerford et al., "$\alpha V\beta 5$ integrin: a co-receptor for adeno-associated virus type 2 infection" *Nat. Med* 5(1):78-82 (Jan. 1999).

Tenenbaum et al., "Tropism of AAV-2 vectors for neurons of the globus pallidus." *Neuroreport* 11(10):2277-2283 (Jul. 14, 2000).

Trybala et al., "Interaction between Pseudorabies Virus and Heparin/Heparan Sulfate." *J. Biol. Chem.* 273(9):5047-5052 (Feb. 27, 1998).

Xiao et al., "Gene Transfer by Adeno-Associated Virus Vectors into the Central Nervous System." *Exp Neurology* 144(1): 113-124 (Mar. 1997).

\* cited by examiner

METHODS OF INCREASING DISTRIBUTION OF NUCLEIC ACIDS

This application claims priority from provisional patent application Ser. No. 60/286,308, filed Apr. 25, 2001 which is hereby incorporated in its entirety by this reference.

FIELD OF THE INVENTION

This invention relates to methods for increasing the volume of distribution of a nucleic acid and/or the pharmacological activity of a therapeutic agent encoded by a nucleic acid using various modes of localized delivery.

BACKGROUND OF THE INVENTION

A variety of localized delivery methods are available, such as convection enhanced delivery (CED) which provides for the distribution of nucleic acids in a homogeneous, targeted fashion to solid tissues in clinically useful volumes. However, the binding of a nucleic acid to binding sites other than the intended target of the nucleic acid limits the volume of distribution ($V_d$).

To overcome this limitation, the present invention provides methods of increasing the volume of distribution of a nucleic acid during various modes of delivery, such as, for example, CED, comprising administering a nucleic acid and a facilitating agent to, for example, a tissue or a subject, whereby the inclusion of the facilitating agent increases the volume of distribution of the nucleic acid. These methods can be utilized to treat a variety of disorders, such as neurodegenerative disorders and cancer.

SUMMARY OF THE INVENTION

The present invention provides a method of increasing the volume of distribution of a nucleic acid comprising a therapeutic agent in a tissue in a subject during localized delivery, comprising administering to the tissue in the subject a nucleic acid comprising a therapeutic agent and a facilitating agent, whereby the inclusion of the facilitating agent increases the volume of distribution of the nucleic acid comprising a therapeutic agent in the tissue.

Further provided by the present invention is a method of treating a neurodegenerative disorder in a subject in need of such treatment, comprising administering to the subject a nucleic acid comprising a therapeutic agent and a facilitating agent, wherein the vector comprising a therapeutic agent and the facilitating agent are administered via localized delivery.

DETAILED DESCRIPTION OF THE INVENTION

Figure 1:
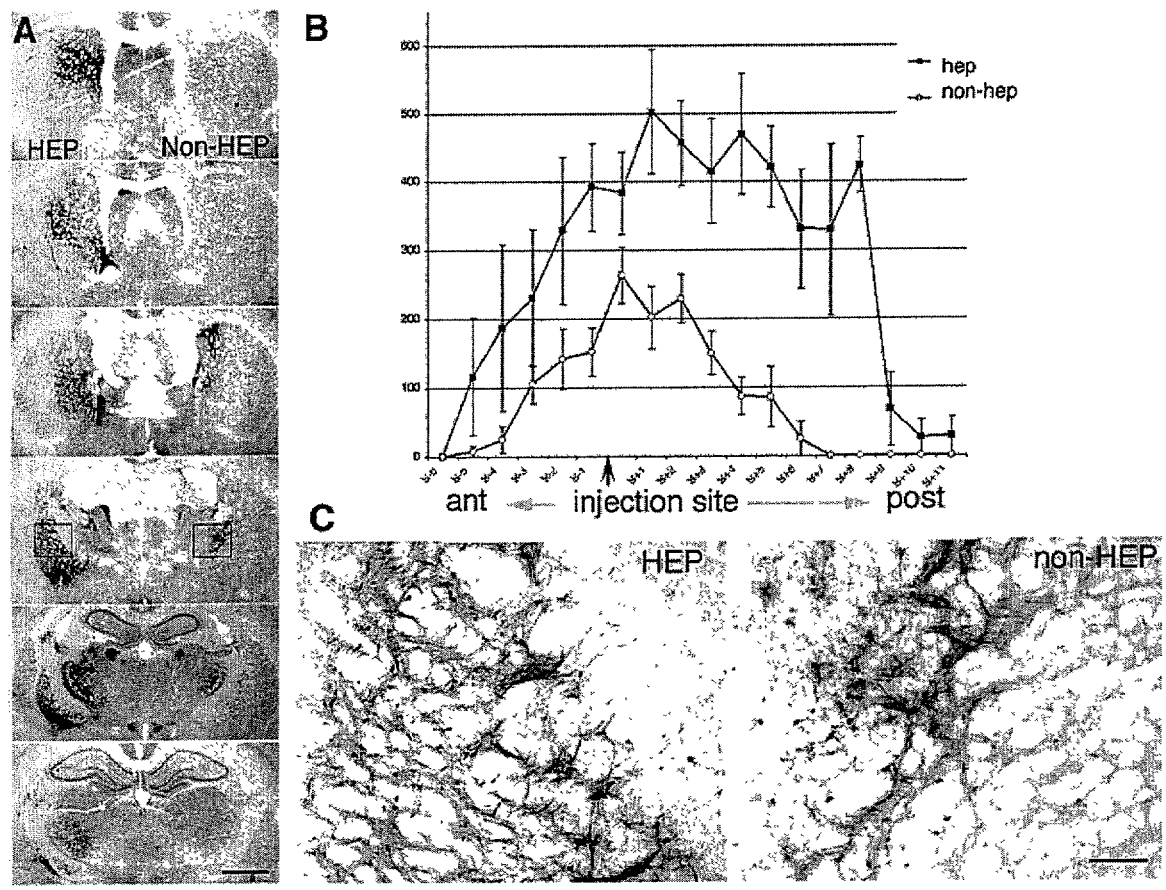
FIG. 1A illustrates that co-infusion with heparin significantly increases the volume of distribution of AAV-2/TK. This figure provides a low power photograph of thymidine kinase immunoreactivity (TK-IR) from a representative animal six days after convection enhanced delivery of 1 µl of viral vector with 1 µl of heparin (left) or with 1 µl of PBS (right). Serial coronal sections (spaced 640 mm) demonstrated significantly extended distribution of gene transfer between the striatum and midbrain in the heparin co-infused side as compared to the non heparin-treated hemisphere (scale bar 1.5 µm).
FIG. 1B shows the quantification of the average (n=6) volume of distribution of thymidine kinase immunoreactivity (TK-IR) using the Cavalieri method. The section label numbers were re-aligned in the bar graph, S-0 represents the injection site. The volume of distribution was significantly higher in the heparin side (o) compared to the non heparin side (two-tailed unpaired t test, p<0.0001). Note the widespread extension of volume of gene transfer in the heparin side, which was 2 to 4 fold higher than on the control side.
FIG. 1C provides a higher power photomicrograph of volume of distribution of AAV-2/TK (boxed regions from 1-A in lateral globus pallidus). The distribution of AAV-2/TK gene transfer was homogenous only on the heparin-treated side (scale bar 130 µm).

The present invention may be understood more readily by reference to the following detailed description of the preferred embodiments of the invention and the Example included herein.

Before the present methods are disclosed and described, it is to be understood that this invention is not limited to specific nucleic acids or specific methods. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise.

The present invention is based on the surprising and unexpected discovery that the volume of distribution of a nucleic acid can be increased during localized delivery. The administration of the nucleic acids of the present invention can be via any localized delivery system that allows for the enhancement of or an increase in the distribution and/or pharmacological activity of a nucleic acid when a facilitating agent is included in the delivery. Examples of such delivery systems include, but are not limited to CED, intraventricular delivery, intracerebroventricular delivery and intracerebral delivery. Examples of other delivery systems include localized injection via hypodermic needle or an injection gun.

The present invention provides a method of increasing the volume of distribution of a nucleic acid comprising a therapeutic agent in a tissue in a subject during localized delivery, such as convection enhanced delivery, localized injection, intraventricular delivery and/or intracerebral delivery, comprising administering to the tissue in the subject a nucleic acid and a facilitating agent, whereby the inclusion of the facilitating agent increases the volume of distribution of the nucleic acid in the tissue.

By "increasing the volume of distribution of a nucleic acid" is meant that the volume of distribution of a nucleic acid, when administered with a facilitating agent is greater than the volume of distribution observed or detected when the nucleic acid is administered in the absence of a facilitating agent. The volume of distribution can be measured as described in the Examples and by methods known in the art. For example, neuroimaging can be used for in vivo detection. Such neuroimaging methods are known in the art and include magnetic resonance imaging (MRI), positron emission topography (PET), single photon emission computed tomography (SPECT) and computed tomography (CT) scan.

As used herein, localized delivery is defined as delivery of a therapeutic agent into a region of the body such as an organ, or a part of an organ. Examples of organs for which localized delivery is suitable include but are not limited to, heart, kidney, liver, brain and lung. Without limiting the invention to this particular example, the brain is an organ that is composed of specific regions or parts defined by either anatomical or physiological function and localized delivery can be to one or more of the specific regions or parts.

Thus, in one embodiment, the nucleic acids and facilitating agents of the present invention can be administered via CED. CED is well established in the art and the skilled artisan would know how to adapt CED protocols in order to deliver a particular combination of nucleic acid and facilitating agent to a solid tissue. U.S. Pat. No. 5,720,720 describes CED and is hereby incorporated by reference in its entirety.

The nucleic acids of the present invention can comprise a nucleotide sequence which functionally encodes a therapeutic agent. To functionally encode the therapeutic agent (i.e., allow the nucleic acid to be expressed), the nucleic acid can include, for example, expression control sequences, such as an origin of replication, a promoter, an enhancer and necessary information processing sites, such as ribosome binding sites, RNA splice sites, polyadenylation sites and transcriptional terminator sequences. Preferred expression control sequences are promoters derived from metallothionine genes, actin genes, immunoglobulin genes, CMV, SV40, adenovirus, bovine papilloma virus, etc. The nucleic acids can be generated by means standard in the art, such as by recombinant nucleic acid techniques, as exemplified in the examples herein and by synthetic nucleic acid synthesis or in vitro enzymatic synthesis.

For example, the nucleic acid comprising a therapeutic agent can be a vector comprising a nucleic acid encoding a therapeutic agent. More specifically, the nucleic acid can be a viral vector comprising a nucleic acid encoding a therapeutic agent. One skilled in the art will appreciate that the viral vector used in the methods claimed herein can comprise any viral vector amenable to delivery to cells and production of the therapeutic agent. For example, the viral vector can be a recombinant adenovirus vector (26), adenoassociated viral vectors (27), lentiviral vectors (28), pseudotyped retroviral vectors (29), vaccinia vectors, and physical transfection techniques (30). This invention can be used in conjunction with any of these or other commonly used gene transfer methods. In a preferred embodiment of the present invention, the specific vector for delivering the nucleic acid encoding a therapeutic agent comprises an adenovirus vector, such as AAV1, AAV2, AAV3, AAV4, AAV5 or AAV6.

As noted above, the viral vector of this invention can be a retrovirus. The retrovirus of this invention can be in the Oncovirinae subfamily of retroviruses, such as HTLV-I or HTLV-II (human T-cell leukemia virus type I and type II, respectively). Additionally, the retrovirus can be in the Lentivirinae subfamily of retroviruses, such as HIV-1, HIV-II, SIV, FIV, EIAV and CAEV (human immunodeficiency virus type I, human immunodeficiency virus type II, simian immunodeficiency virus, feline immunodeficiency virus, equine infectious anemia virus, and caprine arthritisencephalitis virus, respectfully).

In an embodiment where the viral vector is an adenovirus, the nucleic acid can comprise an entire wild-type adenoviral genome or a mutant thereof, or a construct wherein the only adenoviral sequences present are those which enable the nucleic acid to be packaged into an adenovirus particle, or any variation thereof. Packageable lengths of nucleic acids for specific therapeutic agents are known in the art. This adenoviral genome can be coupled with any desired nucleic acid insert, such as an antitumorigentic protein, such that the adenoviral genome, when packaged into an adenovirus particle, also packages the nucleic acid insert. One skilled in the art will appreciate that the nucleic acid insert combined with the adenoviral nucleic acid will be of a total nucleic acid length that will allow the total nucleic acid to be packaged into an adenovirus particle.

In the methods of the present invention, the facilitating agent can be administered prior to administration of the nucleic acid, after administration of the nucleic acid and/or simultaneously with the administration of the nucleic acid. Furthermore, one or more facilitating agents can be administered with one or more nucleic acid.

The present invention also provides a method of increasing the pharmacological activity of a therapeutic agent in a tissue in a subject comprising administering to the tissue in the subject a nucleic acid encoding a therapeutic agent and a facilitating agent, by localized delivery, such as CED, localized injection, intraventricular delivery and/or intracerebral delivery, whereby the inclusion of the facilitating agent increases the pharmacological activity of the therapeutic agent in the tissue of the subject. Pharmacological activity can be measured by methods known in the art.

As used herein, the term "pharmacological activity" refers to the inherent physical properties of a therapeutic agent encoded by a nucleic acid of the present invention. These properties include, but are not limited to, binding properties, half-life, stability, ability to effect signal transduction and other pharmacokinetic properties which would be known to one skilled in the art. On skilled in the are would know how to measure pharmacological activity according to methods known in the art. Methods such as those provided in Bankiewicz et al., 2000 (3) hereby incorporated herein by this reference in its entirety, are suitable for such measurements.

The therapeutic agents of the present invention can include, but are not limited to, antisense oligonucleotides, ribozymes, proteins, drugs, antibodies, antibody fragments, immunotoxins, chemical compounds, protein fragments and toxins.

The facilitating agent, as used herein, can be any agent that increases the volume of distribution of a nucleic acid and/or increases the pharmacological activity of a therapeutic agent encoded by a nucleic acid of this invention. The facilitating agents of the present invention can include, but are not limited to, proteins, drugs, antibodies, antibody fragments, chemical compounds, toxins and protein fragments.

For example, if it is desirable to administer a nucleic acid encoding a therapeutic agent to the brain and the skilled artisan knows or has determined that, in addition to interacting with its target binding site, a given nucleic acid encoding a therapeutic agent interacts with an alternate binding site, a facilitating agent would be administered either before, after and/or simultaneously with the administration of the nucleic acid encoding a therapeutic agent. The facilitating agent would interact with the alternate binding site in order to prevent binding of the nucleic acid encoding a therapeutic agent to this alternate binding site, and thus allow the nucleic acid encoding a therapeutic agent to interact preferentially with the target binding site, thereby resulting in increased volume of distribution of the nucleic acid and/or increased pharmacological activity of the therapeutic agent encoded by the nucleic acid.

Similarly, if one skilled in the art knows or has determined that a nucleic acid encoding a therapeutic agent interacts with a target binding site as well as with a binding protein, a facilitating agent, such as an antibody to the binding protein, would be administered either before, after and/or simultaneously with, the administration of the nucleic acid encoding a therapeutic agent in order to prevent the nucleic acid encoding a therapeutic agent from interacting with the binding protein, and thus allow the nucleic acid encoding the therapeutic agent to interact preferentially with the target binding site thereby resulting in increased volume of distribution of the nucleic acid and/or increased pharmacological activity of the therapeutic agent encoded by the nucleic acid. Because there are numerous types of interactions that can be disrupted by a facilitating agent in order to increase distribution of a nucleic acid and/or increase pharmacological activity of a therapeutic agent encoded by a nucleic acid, the above-mentioned examples are only exemplary and are not meant to limit the present invention in any way.

One skilled in the art could determine the appropriate combination of a nucleic acid encoding a therapeutic agent and a facilitating agent. For example, as described in the Examples herein, heparin can be used as a facilitating agent for the delivery of a an AAV vector encoding a therapeutic agent. Agents that mimic heparin can also be utilized as facilitating agents to deliver an AAV vector or other vectors encoding therapeutic agents that interact with heparin receptors. Therefore, once a particular facilitating agent is identified, other drugs, compounds, proteins, antibodies etc., that mimic that particular facilitating agent can be utilized in the methods of the present invention.

The methods of the present invention can be utilized to deliver nucleic acids encoding therapeutic agents and facilitating agents to tissues such as the brain, heart, lung, solid tumors, liver, kidney, muscle and/or any other tissue in a subject. One skilled in the art could also utilize the methods of the present invention to administer therapeutic agents to tissues in vivo or ex vivo according to standard methods. For example, prior to transplantation, a nucleic acid encoding a therapeutic agent and a facilitating agent can be administered to a tissue to be transplanted to reduce immune rejection of the tissue upon subsequent transplantation in a subject. For example, a nucleic acid encoding VEGF (vascular endothelial growth factor) and its homologs or encoding HGF (hepatocyte growth factor) can be delivered with heparin as a facilitating agent prior to transplantation.

For either ex vivo or in vivo use, the nucleic acids encoding therapeutic agents and facilitating agents of this invention can be administered at any effective concentration. An effective concentration of a nucleic acid encoding a therapeutic agent is one that results in decreasing or increasing a particular pharmacological effect. An effective concentration of a facilitating agent is an amount that results in increasing the volume of distribution of the nucleic acid and/or increasing the pharmacological activity of a therapeutic agent encoded by the nucleic acid as compared to the volume of distribution and/or pharmacological activity of the nucleic acid encoding a therapeutic agent in the absence of the facilitating agent. One skilled in the art would know how to determine an effective concentration according to methods known in the art, as well as provided herein. For example, for a particular tissue to be targeted, cells from the target tissue are biopsied and optimal dosages for delivery of the nucleic acid encoding a therapeutic agent and facilitating agent into that tissue to achieve the desired distribution volume and/or pharmacological activity of the therapeutic agent are determined in vitro, allowing for the optimization of the in vivo dosage of the respective agents, including concentration and time course of administration.

Dosages of the nucleic acids and facilitating agents of this invention will depend upon the disease or condition to be treated and the individual subject's status (e.g., species, weight, disease state, etc.) Dosages will also depend upon the form of the nucleic acids and facilitating agents being administered and the mode of administration. Such dosages are known in the art or can be determined as described above. Furthermore, the dosage can be adjusted according to the typical dosage for the specific disease or condition to be treated. Often a single dose can be sufficient; however, the dose can be repeated if desirable. The dosage should not be so large as to cause adverse side effects. Generally, the dosage will vary with the age, condition, sex and extent of the disease in the patient and can be determined by one of skill in the art according to routine methods (see e.g., Remington's Pharmaceutical Sciences (33)). The dosage can also be adjusted by the individual physician in the event of any complication.

The nucleic acid and/or the facilitating agent of this invention can typically include an effective amount of the respective agent in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained.

It is contemplated that the methods of the present invention can be utilized to treat solid tumors, for example, by administering a nucleic acid encoding an antitumorigenic agent and a facilitating agent during localized delivery into the tumor, such as localized injection, CED, intracerebral delivery and/or intraventricular delivery. An effective combination of a nucleic acid encoding an antitumorigenic agent and a facilitating agent is that combination that results in partial or total killing, reduction in size, disappearance, inhibition of growth, inhibition of vascularization, inhibition of cellular proliferation, an induction in dormancy or an apparent induction of dormancy, and/or a decreased metastasis of a tumor or a tumor cell. These mechanisms of action are only exemplary of the ways an antitumorigenic protein can treat a tumor. The subjects to be treated by the methods of this invention can include subjects undergoing additional anti-tumor therapy, which can include patients undergoing surgery, chemotherapy, radiotherapy, immunotherapy or any combination thereof. Examples of chemotherapeutic agents include cisplatin, 5-fluorouracil and S-1. Immunotherapeutic methods can include administration of interleukin-2 and interferon-.

The present invention further provides a method of treating a neurodegenerative disorder in a subject in need of such treatment, comprising administering to the subject a nucleic acid encoding a therapeutic agent and a facilitating agent, wherein the nucleic acid and the facilitating agent are administered via localized delivery such as convection enhanced delivery, localized injection, intracerebral delivery and/or intraventricular delivery. Other means of localized delivery include catheterization of an artery in the brain in order to supply agents such as mannitol or other sugars that are capable of disrupting the blood-brain-barrier to allow delivery of nucleic acids encoding therapeutic agents and facilitating agents.

The neurodegenerative disorders that can be treated by the methods of the present invention include, but are not limited to, Parkinson's disease, Huntington's disease, Alzheimer's disease, ALS (amylotrophic lateral sclerosis), PSP (progressive supranuclear palsy), MSA (multiple system atrophy), SCA (autosomal dominant spinocerebellar ataxia) and other cerebellar ataxias. Since the methods of the present invention can be utilized to transduce nucleic acids at one location and use axonal transport to deliver the nucleic acid and its subsequent product into projection regions of the brain, this invention provides a way to supply large cortical areas with nucleic acids. The methods of the present invention can also be used for transduction of the spinal cord.

For example, in a method of this invention employing intraventricular delivery, a catheter can be implanted in the ventricle of a subject diagnosed with a neurodegenerative disorder such that the appropriate nucleic acid comprising a therapeutic agent and facilitating agent can be injected into the ventricle via the catheter. Dosages will depend upon the disease or condition to be treated, and the individual subject's condition. Dosages will also depend upon the material being administered. Such dosages are known in the art or can be determined as described above. Furthermore, the dosage can be adjusted according to the typical dosage for the specific disease or condition to be treated. Often a single dose can be sufficient; however, the dose can be repeated if desirable. The dosage should not be so large as to cause adverse side effects. Generally, the dosage will vary with the age, condition, sex and extent of the disease in the subject and can be determined by one of skill in the art. The dosage can also be adjusted by the individual physician in the event of any complication. For guidance on intraventricular delivery, see (31), which is hereby incorporated herein by this reference in its entirety.

The invention further provides a method of treating a lysosomal storage disorder in a subject in need of such treatment, comprising administering to the subject a nucleic acid encoding a therapeutic agent and a facilitating agent, wherein the nucleic acid and the facilitating agent are administered via localized delivery, such as convection enhanced delivery, intracerebral injection or intraventricular delivery.

Examples of lysosomal storage disorders that can be treated by the methods of this invention include, but are not limited to, Gaucher disease, Krabbe disease, Fabry disease, Tay-Sachs disease, Niemann-Pick disease type A/B, Niemann-Pick disease type C, Farber disease, neuronal ceroid lipofuscinosis (infantile), neuronal ceroid lipofuscinosis (late infantile), Schindler disease, metachromatic leukodystrophy, Pompe disease and Sandhoff disease (32).

The following examples are set forth so as to provide those of ordinary skill in the art with a complete disclosure and description of how the methods claimed herein may be performed, and are intended to be purely exemplary of the invention and are not intended to limit the scope of what the inventors regard as their invention.

EXAMPLE I

In vivo Gene Delivery

Six female Sprague-Dawley rats (250–300 g) from Charles River Laboratories (Wilmington, Mass.) were maintained and cared for according to the National Institutes of Health Guide for the Care and Use of Laboratory Animals. Under deep isofluorane anesthesia, rats were placed in a stereotactic frame (David Kopf Instrument, Tujunga, Calif.) and a midline incision was made to expose the cranium. A burr hole was made in the skull at AP=0 mm and L=+/−3 mm from bregma (Paxinos and Watson's atlas of rat brain) [17] using a small dental drill. The infusion was performed using a convection enhanced delivery method as described elsewhere [3,15]. The cannula was inserted bilaterally in the striatum to the depth of 4 mm and a total volume of 2 μL was administered at a rate of 0.5 μl/min using a micro infusion pump (CMA/100). One μl ($1.3 \times 10^9$ particles) of AAV-2/TK was mixed with either 1 μl of heparin (10K units/ml, Elkins Sinn, Inc-Cheery Hill, N.J.) or 1 μl of sterile PBS. For direct comparison, both solutions were injected in all animals, heparin AAV-2/TK on the left and non-heparin AAV-2/TK on the right side.

Construction of pTK1

The pTK1 plasmid was constructed by placing the herpes simplex virus thymidine kinase gene (HSV1/TK) under the transcriptional control of the cytomegalovirus (CMV) immediate early promoter. An intron sequence comprised of a CMV splice donor and globin splice acceptor was located directly upstream of the TK gene and the human growth hormone polyadenylation sequence (hGH poly A) was placed downstream. The entire sequence was flanked by AAV-2 inverted terminal repeats (ITRs) that are required for vector replication and packaging. The construct was propagated in a Kanscript-based plasmid. The pTK1 was used in the production of AAV-2/TK. Recombinant AAV-2 virions (AAV-2/TK) were produced in human embryonic kidney 293 cells using an adenovirus-free system originally described by Matsushita [16] with modifications described in Bankiewicz et al [3]. Vector titer was $1.3 \times 10^{12}$ particles/ml as determined by quantitative dot-blot hybridization.

Immunohistochemistry.

Six days following surgery, rats were overdosed with pentobarbitol (50 mg/kg) and perfused transcardially with PBS followed by 4% paraformaldehyde. Brains were post-fixed in paraformaldehyde for 1 hour and transferred to 30% sucrose for 48 hours at 4° C. After being equilibrated in sucrose, the brains were frozen in cold isopentane, sectioned at 40 μm thickness and serially collected in the vial. Fourteen to 18 sections (every eighth) spanning the area of gene transfer, from 1 mm anterior to the injection site, towards the midbrain were stained for TK-IR.

Free-floating sections were incubated in 3% $H_2O_2$ for 30 minutes to block endogenous peroxidase activity. After blocking in goat serum for one hour (0.5% goat serum 0.005% Triton X-100 in PBS), sections were incubated overnight with anti-TK antibody (1:1000, Yale University). After washing, sections were reacted with biotinylated goat-anti rabbit IgG (Vectors lab) at room temperature for 1 hour. The biotinylated complex was then visualized with streptavidin horseradish peroxidase 1:300 (Vector Labs, Burlingame, Calif.) using DAB (Vectors lab, Burlingame) as a chromogen. Sections were mounted on gelatinized slides, dehydrated in ascending series of alcohol, cleared in xylene and cover slipped in mounting medium Cytoseal (Stephens, Scientific, Riverdale, N.J.).

Double immunofluorescence staining was performed on four separate series. TK positive cells were stained using the same rabbit IgG primary antibody (1:100) followed by a rhodamine conjugated goat anti-rabbit antibody (1:100, Jackson Immunoresearch). Series were stained simultaneously for TK and either NeuN, a neuronal nuclear marker (mouse monoclonal, 1:250, Chemicon) or glial fibrillary acid protein (GFAP) (mouse monoclonal, 1:250, Chemicon) followed by a secondary FITC conjugated goat anti-mouse antibody (1:100, Jackson Immunoresearch). The staining procedure was the same as described above except that the hydrogen peroxide and visualization steps were omitted. These sections were examined for co-localized staining and photographed using a Zeiss Confocal LSM 510 station.

Appropriate controls were processed simultaneously without primary antibody. Quantitative measurement of gene distribution The volume of distribution was estimated in serial sections (every eighth) using the Cavalieri method [7] under 2.5× magnification in a Leitz microscope equipped with a 3CCD video camera (Sony, Japan) and stereology software (Neurozoom, La Jolla, Calif.). The total volume of the rat striatum (from AP+0.2 to –0.8, according to Paxinos atlas) and external globus pallidum (from AP –0.8 to –1.8, according to Paxinos atlas) was calculated using the same procedure, to determine the percent of transfected volume for each nucleus. To compare the distribution, sections were aligned according to the injection site independently for each side: the section in which the injection track and site were most clearly identified was considered section 0 (S-0) for each side. Results are expressed as mean and SEM. A two-tailed unpaired t-test was used to compare left (heparin) to right (non-heparin) distribution of TK-IR.

Administration of AAV-2/TK resulted in robust gene expression in the basal ganglia and other subcortical regions of the rat brain. The area showing gene expression was markedly expanded on the side of the brain that was treated with heparin in all animals extending to 5.4 mm vs 3.8 mm in the non-heparin side (FIG. 1-A). The estimated volume of distribution of gene transfer was significantly higher on the heparin side, at every level exceeding 3–4 times that of the control side (p<0.0001, FIG. 1-B). At the injection site, TK-IR was very dense on the non-heparin side but the volume was still higher on the heparin treated side (1.8 times) suggesting that in the absence of heparin most AAV-2 particles attach to cells in the vicinity of the needle track. On the heparin co-infused side, TK-IR was present beyond the needle track region and extended from the rostral striatum to midbrain regions (FIG. 1-A). Using volumetric measurement it was estimated that, on the heparin co-infused side, cells expressing TK covered about 50% of the striatal volume, while less than 20% of the striatum expressed TK-IR on the control side. AAV-2/TK infusion with heparin resulted in TK-IR of 100% of the globus pallidus expressing TK-IR, while less than 70% was positive on the contralateral side (FIG. 1-A). TK-IR was also detected caudal to the globus pallidus and was present in the external medullary lamina and thalamus (FIG. 1-A).

The pattern of gene transfer was different between the two sides. On the heparin co-infused side TK-IR appeared more diffuse than on the contralateral side, where dense TK-R staining was present close to the infusion site with a sharp demarcation to striatal tissue with no gene expression (FIG. 1-C) Independent from the use of heparin, the majority of cells that were transfected by AAV-2/TK appeared to have neuronal morphology confirmed by co-localization of the neuronal marker NeuN with TK in transfected cells. Confocal images showed colocalization of NeuN (red channel) and TK (green channel). Double staining of the striatum shows the identification of neuronal morphology using double staining with TK (antibody titer 1:100) and neuronal marker (NeuN antibody titer 1:250). Every TK positive cell in both the heparin and non heparin side was NeuN positive. None of the TK-IR cells expressed the glial marker GFAP in the striatum although occasional TKIR glial cells have been observed along the needle track in cortex. This was seen by double staining with TK (red channel) and GFAP (astrocyte marker, green channel) which did not show astrocytes transfected by AAV-2/TK in the striatal area. Neither lymphocytic infiltration or perivascular cuffing was detected on either side, that would suggest a gross immune response of the host in response to TK gene transfer. The cannula track was associated with the minor presence of hemosiderin that was comparable between the two sides. No major bleeding was observed on the heparin co-infused side.

Combining convective delivery with heparin produced widespread expression of TK-IR. Heparin reduced attachment of AAV-2 particles to the cells and ECM. The lower density of TK-IR cells in the vicinity of the needle tract indicates that more viral particles move further away from the infusion site in the presence of heparin. In contrast, regions of the brain infused with AAV-2, without heparin, showed very dense clusters of transduced cells close to the infusion site and a lower volume of distribution, as AAV-2 particles became bound to the ECM and cells. This binding prevented AAV-2 from reaching remote regions of the brain and resulted in a sharp decline of gene transfer at the margins of detectable gene expression. Consistent with this observation, areas close to the infusion site, where high levels of AAV-2 particles are present, exhibit a high level of gene transfer. In this study, the presence of heparin enhanced the volume of gene transfer by 4-fold and resulted in more uniform gene expression.

The dose of heparin used in this experiment was very small (10U) and did not result in hemorrhage or cell damage. A combination of heparin and AAV-2 titer per volume can be optimized for the region and type of tissue to be targeted by CED of the AAV vector.

Similarly, other vector systems appear to use heparan sulfate proteoglycan as a binding site [8,12,24]. Therefore, heparin with its effect as a competitor for heparan sulfate proteoglycan receptors can be used to improve gene delivery via different vector systems. The inhibitory effect of a small dose of heparin during microinfusion does not affect the capacity of the viral particles to infect the cells. Furthermore, the transient effect of heparin in the extracellular matrix can temporarily inhibit the attachment of viral particles to the cell surfaces of the neurons bordering the infusion site.

Another advantage of co-infusion of heparin with viral particles is that the number of viral particles injected can potentially be reduced while still obtaining optimal distribution of the particles in the targeted brain structure.

The present invention demonstrates the advantages of using heparin in combination with CED to enhance distribution and expression of AAV-2 viral particles in large areas of the brain. Due to more efficient gene transfer using convectionenhanced delivery combined with heparin co-administration, lower number of viral particles may be used to efficiently deliver therapeutic genes to brain. This approach is applicable for treating a variety of human brain disorders including brain tumors and neurodegenerative diseases.

EXAMPLE II

Experimental Subjects

The protocol was reviewed and approved by the Institutional Animal Care and Use Committee. Four rhesus monkeys (3–5 kg) were lesioned with MPTP according to Bankiewicz et al. (3, 32, 33). The experimental design included unilateral intracarotid artery (ICA) (2.5–3.5 mg—right side) plus four iv administrations of 0.3 mg/kg doses of MPTP-HCl that produces a nearly complete dopaminergic lesion on the side of the carotid artery (CA) infusion (ipsilateral side) and a partial lesion on the other side of the brain (contralateral side). CED of either AAV with reporter (lacZ) (n=2) or therapeutic genes (AADC) (n=2) to the ipsilateral striatum was subsequently performed. Three additional control monkeys received AAV-TK injections into the right and left putamen. The right side injection was made with heparin.

Surgical Procedures

Preparation of Loading Lines: In the surgery room, a sterile field was created to prepare the infusion system. Infusion cannulae were flushed with saline to assess the integrity between the needle and tubing interface. Sterile infusion cannulae and loading lines were connected using the appropriate fittings with extreme caution taken to prevent the collection of air bubbles in the system. Oil infusion lines were prepared and 1 ml gas tight Hamilton syringes filled with oil were attached to a Harvard infusion pump. Six infusion cannulae were fitted onto holders (3 cannulae per holder) and mounted onto a stereotactic tower. Following the union of the oil and loading lines, the needle cannulae were primed with AAV and the infusion system transferred to the surgery table. Initial infusion rates were set at 0.1 µl/min; the lines visually inspected to ensure a smooth flow of fluid through the system, and the cannulae manually lowered to their target sites.

Cannula Design: The cannula system consisted of three components: (i) sterile infusion cannula; (ii) sterile loading line housing AAV-DDC or AAV-LacZ; and (iii) a nonsterile infusion line containing olive oil. The infusion cannula consisted of 27 G needles (outer diameter, 0.03"; inner diameter, 0.06"; Terumo Corp., Elkton, Md.) fitted with fused silica (outer diameter, 0.016", inner diameter, 0.008"; Polymicro Technologies, Phoenix, Ariz.), and placed in Teflon tubing (0.03" ID, Upchurch Scientific, Seattle, Wash.) such that the distal tip of the silica extended approximately 15 mm out of the tubing. The needle was secured into the tubing using superglue and the system was checked for leaks prior to use. At the proximal end of the tubing, a Tefzel fitting and ferrule were attached to connect the adjacent loading line. Loading and infusion lines consisted of 50 cm sections of Teflon tubing (outer diameter: 0.062"; inner diameter: 0.03") fitted with Tefzel $\frac{1}{16}$" ferrules, unions, and male Luer-lock adapters (Upchurch Scientific, Oak Harbor, Wash.) at the distal ends. The sterile loading lines accommodated up to a 1000 µl volume and were primed with saline prior to use.

Intrastriatal Infusion of AAV

The animals were initially sedated with Ketamine (Ketaset; 10 mg/kg, I.M.), intubated and prepped for surgery. A venous line was established using a 22-gauge catheter positioned in the cephalic or saphenous vein to deliver isotonic fluids at 5–10 ml/kg/hr. Isoflurane (Aerrane, Omeda PPD Inc., Liberty, N.J.) was delivered at 1–3% until the animal maintained a stable plane of anesthesia. The head was placed in an MRI-compatible stereotactic frame according to preset values attained during a baseline MRI scan. Vital signs were monitored. A sterile field was created and a midline incision performed through the skin, muscle and fascia using electrocautery (Surgistat Electrosurgery, Valleylab Inc., Boulder, Colo.). Gentle retraction of fascia and muscle allowed for cranial exposure over cortical entry sites. A unilateral craniotomy was performed using a Dremel dental drill to expose a 3 cm×2 cm area of dura mater above the target sites. Multiple needle cannulae attached to a holder were stereotactically guided to striatal target sites. Two sites in caudate and 4 sites in each putamen were targeted. 30 µl of AAV were infused in each site at 0.1 and 0.2 µl/min for 60 min followed by 30 min infusion at 0.4 µl/min. $3.6 \times 10^{11}$ of AAV-AADC or $1.5 \times 10^{11}$ of AAV-LacZ (total particles) were administered into each monkey. Approximately 15 min following infusion, the cannulae assembly was raised at a rate of 1/mm/min until it was out of the cortex. The cortex was rinsed with saline, bone margins trimmed with ronguers and the wound site closed in anatomical layers. Animals were monitored for full recovery from anesthesia, placed in their home cages and clinically observed (2×/day) for 5 days following surgery. Total neurosurgery time was 4.5 hr per animal.

AAV Vector Production

The HEK 293 cell line was cultured in complete DMEM (BioWhittaker) containing 4.5 g/liter glucose, 10% heat-inactivated fetal calf serum (FCS), and 2 mM glutamine at 37° C. in 5%$CO_2$ in air. 40 T225 flasks were seeded with $2.5 \times 10^6$ cells each and grown for 3 days prior to transfection to 70–80% confluency (approximately $1.5 \times 10^7$ cells per flask). The transfection and purification methods (16,34) were employed for AAV vector production, with minor modifications. The vector production process involved co-transfection of HEK 293 cells with 20 µg of each of the following three plasmids per flask: the AAV-AADC plasmid, the AAV helper plasmid (pHLP19, containing the AAV rep and cap genes), and the adenovirus helper plasmid (pladeno-5, previously known as pVAE2AE4-2 and composed of the E2A, E4, and VA RNA genes derived from purified adenovirus-2), using the calcium phosphate method for a period of 6 hr. After transfection, the media was replaced and the cells were harvested 3 days later. Cell pellets were then subjected to 3 cycles of freeze-thaw lysis (alternating between dry ice-ethanol and 37° baths with intermittent vortexing). The cell debris was removed by centrifugation (10,000 g for 15 min). Supernatant was centrifuged a second time to remove any remaining turbidity and subsequently treated with Benzonase$^R$ (200 µ/ml) at 37° C. for 1 hr to reduce contaminating cellular DNA. Following incubation, the supernatant was made and placed on ice for 1 hr. The resulting precipitate was removed by centrifugation (10,000 g for 15 min.) and discarded. The supernatant was then made (10% in PEG (8000)), and was placed on ice for 3 hr. Precipitate was collected by centrifugation (3000 g for 30 min) and resuspended in 4 ml of 50 mM Na-HEPES, 0.15 M NaCl, 25 mM EDTA (pH 8.0) per 20 T225 flasks. Solid CsCl was added to produce a density of 1.4 g/ml and the sample was centrifuged at 150,000 g for 24 hr in a Beckman T170 rotor. AAV-containing fractions were pooled, adjusted to a density of 1.4 g/ml CsCl, and centrifuged at 350,000 g for 16 hr in a Beckman NVT65 rotor. The fractions containing AAV were then concentrated and diafiltered against excipient buffer (5% sorbitol in PBS). The titer of the purified AAV-AADC vector was determined using quantitative dot blot analysis and vector stocks were stored at −80° C.

Construction of AAV-AADC Plasmid

A 1.5 kb BamHI/PvuII human AADC cDNA (courtesy of Dr. Keiya Ozawa, Jichi Medical School, Tochigi, Japan) was cloned into the AAV expression casette pV4.1c at BamHI/HindII sites. The expression casette contained a CMV promoter, a chimeric intron composed of a CMV splice donor and a human globin splice acceptor site, human growth hormone polyadenylation sequence, and flanking AAV ITRs (inverted terminal repeats) (19).

Construction of AAV-TK Plasmid

The pTK1 plasmid was constructed by placing the herpes simplex virus thymidine kinase gene (HSV1 TK) under the transcriptional control of the cytomegalovirus (CMV)

immediate early promoter. An intron sequence made up of a CMV splice donor and a β-globin splice acceptor was located directly upstream of the TK gene and the human growth hormone polyadenylation sequence (hGH poly A) was placed downstream. Sequence from bacterial β-galactosidase (LacZ spacer) was also placed downstream of the expression casette to achieve optimal viral packaging size. The entire sequence was flanked by AAV inverted terminal repeats (ITRs) that are required for vector replication and packaging. The construct was propagated in a Kanscript-based plasmid. pTK1 was used in the production of AAV-TK.

Histological Procedures

Animals were deeply anesthetized with sodium pentobarbital (25 mg/kg i.v.) and sacrificed 8 weeks following AAV-AADC and AAV-lacZ administration and 4 weeks following AAV-TK administration. The brains were removed and placed in the brain matrix, and sectioned coronally into 3–6-mm slices. One 3-mm thick striatal brain slice from each monkey was immediately frozen in –70° C. isopenthane and stored frozen for histological analysis. The remaining 6 mm thick slices were post-fixed in formalin for 72 hr, washed in PBS for 12 hr and adjusted in an ascending sucrose gradient (10–20–30%) and frozen.

The formalin-fixed brain slices were cut into 30 μm thick coronal sections in a cryostat. Sections were collected in series starting at the level of the rostral tip of the caudate nucleus all the way caudally to the level of the substantia nigra. Each section was saved and kept in antifreeze solution at –70° C. Sections were post-fixed in formalin for 15 min and processed for immuno-cytochemistry and thionine staining. Serial sections were stained for aromatic amino dopa decarboxylase (ADDC), LacZ or thymidine kinase (TK) immunoreactivity (IR). Every 12$^{th}$ section was washed in phosphate buffered saline (PBS) and incubated in 3% $H_2O_2$ for 20 min to block the endogenous peroxidase activity. After washing in PBS, the sections were incubated in blocking solution (10% normal goat serum and 0.1% Triton-X 100 in PBS) for 30 min, followed by incubation in primary antibody solution—ADDC (rabbit polyclonal, Chemicon, 1:2000) or B-gal (rabbit polyclonal, Cortex Biochem, 1:5000) TK (a gift from Dr. William Summers, Yale University, 1: 1000) for 24 hr. The sections were then incubated for 1 h in biotinylated anti-rabbit IgG secondary antibody (Vector Labs, 1:300). The antibody binding was visualized with streptavidin horseradish peroxidase (Vector Labs, 1:300) and DAB chromogen with nickel (Vector Labs). Sections were then coverslipped and examined under a light microscope.

Stereological Analysis of AAV-TK Infected Cells

Quantitative estimates of TK positive neurons within the substantia nigra, thalamus and globus pallidus were determined using a stereological system consisting of a computer-assisted image analysis system, including a Leitz Otholux II microscope hard-coupled to a Prior H128 computer-controlled x-y-z motorized stage, a high sensitivity Sony 3CCD video camera system (Sony, Japan) and a Macintosh G-3 computer. All analyses were performed using NeuroZoom software (La Jolla, Calif.). Prior to each series of measurements, the instrument was calibrated. From one to eight sections were counted from each structure. The region of TK positive neurons was outlined at low magnification (2.5× objective) and from 25% to 100% of the outlined region was measured with a systematic random design of dissector counting frames (80340 μm$^2$) using a 10× plan apochromat objective with a 0.25 numerical aperture. The average thickness of the sections was measured at 30 μm but neurons were counted within a 20 μm height of tissue, with a guard height of 5 μm at the top and at the bottom of each section. The number of neurons was expressed per mm$^2$.

Tissue Distribution

To determinate the distribution of AADC, lacZ and TK positive cells in the striatum as well as at other locations distant from the striatum, immunohistochemical stainings were performed. AADC, lacZ and TK positive cells were observed in the striatum (caudate and putamen). TK positive cells were present beginning from the level of the shell of the nucleus accumbens and ending on the level of the caudal anterior commisurae and they covered about 80% of the putamen. The area with TK positive cells in the striatum was larger on the heparin treated side compared to the side without heparin. The positive cells were also present in the external and internal part of the globus pallidus (AADC, lacZ, TK), in the compacta, the lateralis and the dorsal part of the substantia nigra (TK, AADC; it was not possible to distinguish endogenous and exogenous AADC), in thalamic nuclei including ventromedial (VM), mediodorsal (MD) and ventral lateral (VL) nuclei. There was no positive staining in subthalamic nucleus. Almost all of the cortical areas including motor, primary somatosensory showed TK positive cells. Neuronal bundles in the internal capsule and anterior commisurae were observed. TK positive cells were also positive for the neuronal marker NeuN, but they were not positive for glial marker GFAP.

Stereological Analysis

Stereological analysis in structures other than striatum of the basal ganglia circuits have shown differences in the infected cell number on the heparin treated compared to the non-heparin treated side. There were more TK positive cells in the globus pallidus on the heparin treated side (28 cells/mm$^2$) compared to the non-heparin treated side (23 cells/mm$^2$). The same result was observed in the thalamus comparing means from 3 monkeys: 34 cells/mm$^2$ on the heparin treated side vs 18 cells/mm on the non-heparin treated side. However, in an analysis of these results obtained from these monkeys separately, in two monkeys there were more cells in the thalamus of the non-heparin treated side but in one monkey the positive cell number in this structure was eight times greater than in the other two. An error due to injection was excluded since the needle tract was not found on any of the slides that were examined. The opposite effect was observed in the compact part of the substantia nigra. There were more TK positive cells on the side not treated with heparin (18 cells/mm$^2$) than on the heparin treated side (9 cells/mm$^2$). The differences were statistically significant.

In this study, the presence of the AAV vector transgene product in neurons of brain structures distant from the delivery place was observed, indicating that the AAV vector undergoes neuronal and transsynaptic transport. This phenomenon was observed after intrastriatal delivery using a CED method as well as after vsimple one needle delivery. Injection of the vector into the striatum allows anterograde, retrograde and transsynaptic transport of the vector to many brain structures. Connections of the striatum with other brain structures form closed circuits called basal ganglia circuits (35). Striatal cells infected by AAV vectors produce protein that is detectable by immunohistochemistry. AAV transgene products L-aminoacid decarboxylase, thymidine kinase and β-galactosidase are the protein enzymes that are not able to cross the cellular membrane and after AAV infection are present only within the infected cells and are not able to be secreted into the synaptic cleft. The positive staining in the structures of basal ganglia circuits indicates that after striatal cell infection, AAV vector is retrogradely transported to the cerebral cortex and is transported via the nigrostriatal pathway to the ventral tegmantal area and the compact part of the substantia nigra. The AAV vector is also anterogradely transported from the striatum to the internal part of the globus pallidus and the reticular part of the substantia nigra via a direct pathway to the external part of the globus pallidus via the indirect pathway and then trans-synaptically to the thalamus, cerebral cortex, striatum, hypothalamus and then to the globus pallidus (35). A viral vector with a transgene is small enough to be incorporated into synaptic vesicles together with neurotransmitters which can then be secreted into the synaptic cleft and undergo internalization to postsynaptic cells together with the neurotransmitter connected to the receptor.

The positive staining was observed in all structures of the basal ganglia circuits after AAV-TK delivery. AADC protein was observed beside the striatum and substantia nigra as well as in the globus pallidus and thalamus. β-galactosidase protein was observed in the globus pallidus. After CED delivery that allows the injected vector solution to be spread within a large area, the amount of the vector in each infected cell is probably smaller than after simple needle delivery and this smaller amount of the vector is transsynaptically transported to nearby brain structures. The observations of AADC and lacZ positive staining in the globus pallidus and thalamus (AADC) and only globus pallidus (lacZ) confirm this. The AAV-AADC vector presence in the striatum and cerebral cortex of both hemispheres after unilateral CED striatal delivery was detected using PCR and Southern blot analysis indicating that vector is able to spread through the brain via hemisphere interconnections as well as cerebrospinal fluid which can be a good medium for virus transport. A similar observation was made with AAV-TK intracranial delivery (6).

An additional aspect of this work is the demonstration of the influence of coinfusion with heparin on the distribution of the AAV vector. The same effect was observed in the experiments described herein since the area of TK positive cells staining in the striatum on the heparin treated side of the brain is greater than on the opposite side. Stereological studies on the structures of the basal ganglia circuits, other than striatum, have shown differences in the infected cell number on the heparin treated compared to the non-heparin treated side. More cells were found in the globus pallidus and thalamus on the heparin treated side, suggesting that more AAV particles are incorporated into the striatal cells on this side. Therefore more particles are anterogradely transported to connected structures. The opposite effect was observed in the compact part of the substantia nigra where AAV particles were transported by retrograde transport by processes of the dopaminergic cells, which bodies are situated in this structure.

Throughout this application, various publications are referenced. The disclosures of these publications in their entireties are hereby incorporated by reference into this application in order to more fully describe the state of the art to which this invention pertains.

REFERENCES

1. Bajetto A, Bonavia R, Barbero S et al. *J Neurochem* 73: 2348–2357(1999)
2. Bankiewicz K S, Leff S E, Nagy D et al. *Ex Neurology* 144:147–156(1997)
3. Bankiewicz K S, Eberling J L, Kohutnicka M et al. *Exp Neurology* 164:2–14(2000)
4. Bemfield M, Gotte M, Park P W et al. *Annu.Rev.Biochem.* 68:729–777 (1999)
5. Betz A L, Shakui P, Davidson B L. *Exp Neurology* 150:136–142 (1998)
6. Bhat S, Spitalkik S, Gonzalez-Scarano F et al. *Proc Natl Acad Sci, USA* 88:7131–7134 (1991)
7. Cavalieri B (1996) In: Geometria degli indivisible, pp.1–543 Torino. Unione Tipografica Editrice.
8. Chung C S, Hsiao J C, Chang Y S et al. *Journal of virology* 72(2): 1577–1585 (1998)
9. Cocchi F, Lopez M, Menotti L et al. *Pro. Natl. Acad.Sci* 95:15700–15705 (1998)
10. Cunningham J, Oiwa Y, Nagy D et al. *Cell transplantation* 9: 585–594 (2000)
11. Dowd C J, Cooney C L, Nugent M A *J Bio Chem* 274 (8): 5236–5244 (1999)
12. Feyzi E, Trybala E, Bergstrom T et al. *J Bio Chem* 272 (40) 24850–24857 (1997)
13. Hamilton J F, Morrison P F, Chen M Y et al. *Exp Neurology* (in press) (2000)
14. Immergluck L C, Domowicz M S, Schwartz N B. *J of Gen Virol* 79(3): 549–559 (1998)
15. Lieberman D M, Laske D W, Morrison P F et al. *J Neurosurgery* 82:1021–1029 (1995)
16. Matsushita T, Ellinger S, Ellinger C et al. *Gene Therapy* 5:938–945 (1998)
17. Paxinos G, Watson C (1997) The rat brain in stereotaxic coordinates
18. Peel A L, Klein R L. *J Neurosci Methods* 98:95–104 (2000)
19. Qing K, Mah C, Hansen J et al. *Nature America Inc* 5(1): 71–77 (1999)
20. Qiu J, Handa A, Kirby M et al. *Virology* 269: 137–147 (2000)
21. Summerford C, Samulski R J. *J Virology* 72(2): 1438–1445 (1998)
22. Summerford C, Bartlett J S, Samulski R J. *Nat Med* 5(1): 78–82 (1999)
23. Tenenbaum L, Jurysta F, Stathopoulos A, et al. *Neuroreport* 11(10): 2277–2283 (2000)
24. Trybala E, Bergstrom T, Spillmann D et al. *J Bio Chem.* 273 (9):5047–5052 (1998)
25. Xiao X, Li J, McCown T J et al. *Exp Neurology* 144: 113–124 (1997)
26. Mitani et al. "Transduction of human bone marrow by adenoviral vector." *Human Gene Therapy* 5:941–948 (1994)
27. Goodman et al. *Blood* 84:1492–1500 (1994)
28. Naidini et al. *Science* 272:263–267 (1996)
29. Agrawal et al. *Exp. Hematol.* 24:738–747 (1996)
30. Schwarzenberger et al. *Blood* 87:472–478 (1996)
31. Kordower et al. *Ann. Neur.* 46: 419–424 (1999)
32. Bankiewicz et al., *Life Sci.* 39: 7-(1986)
33. Bankiewicz et al. *Curr. Protoc. Neurosci.* 9.4.1–9.4.32 (1999).
34. Herzog et al. *Nat. Med.* 5: 56–63 (1999).
35 Gerfen C. R., and Wilson, C. J. *Handbook of Chemical Neuroanatomy*, Vol. 12: *Integrated Systems of the CNS*, Part III. 371–468 (1996).

What is claimed is:

1. A method of treating Parkinson's disease in a subject in need of such treatment, comprising administering to the subject an AAV-2 vector comprising a nucleic acid sequence encoding aromatic amino acid decarboxylase (AADC) and heparin, wherein the nucleic acid is operably linked to a promoter, and wherein the nucleic acid encoding AADC and heparin are administered via localized delivery.

2. The method of claim 1, wherein the localized delivery is selected from the group consisting of convection enhanced delivery, hypodermic injection, intracerebral injection and intraventricular injection.

* * * * *